United States Patent
Gerhardt et al.

(10) Patent No.: US 8,679,333 B2
(45) Date of Patent: *Mar. 25, 2014

(54) CLOSED LOOP FLOW CONTROL OF A HPLC CONSTANT FLOW PUMP TO ENABLE LOW-FLOW OPERATION

(75) Inventors: Geoff C. Gerhardt, Millbury, MA (US); Joseph A. Luongo, Walpole, MA (US)

(73) Assignee: Waters Technologies Corporation, Milford, MA (US)

( * ) Notice: Subject to any disclaimer, the term of this patent is extended or adjusted under 35 U.S.C. 154(b) by 1062 days.

This patent is subject to a terminal disclaimer.

(21) Appl. No.: 12/692,795

(22) Filed: Jan. 25, 2010

(65) Prior Publication Data

US 2010/0116745 A1    May 13, 2010

Related U.S. Application Data

(62) Division of application No. 11/569,301, filed as application No. PCT/US2005/017923 on May 20, 2005, now Pat. No. 7,674,375.

(60) Provisional application No. 60/573,528, filed on May 21, 2004.

(51) Int. Cl.
  *B01D 15/08* (2006.01)
(52) U.S. Cl.
  USPC ......... 210/198.2; 210/101; 210/656; 210/659
(58) Field of Classification Search
  USPC ................... 210/656, 69, 101, 198.2; 422/70
  See application file for complete search history.

(56) References Cited

U.S. PATENT DOCUMENTS

| | | |
|---|---|---|
| 3,917,531 A | 11/1975 | Magnussen |
| 5,360,320 A | 11/1994 | Jameson et al. |
| 5,456,124 A | 10/1995 | Colvin |
| 5,738,783 A | 4/1998 | Shirota et al. |
| 5,837,903 A | 11/1998 | Weigand |
| 6,402,946 B1 | 6/2002 | Spraul et al. |
| 6,627,075 B1 | 9/2003 | Weissgerber et al. |
| 6,712,085 B2 | 3/2004 | Weissgerber et al. |
| 7,186,336 B2 | 3/2007 | Gerhardt et al. |
| 2005/0109698 A1 | 5/2005 | Gerhardt et al. |

FOREIGN PATENT DOCUMENTS

| | | |
|---|---|---|
| JP | 64-088361 | 3/1989 |
| WO | 2004027535 | 4/2004 |

OTHER PUBLICATIONS

Translation of Notice of Rejection, for Japanese Patent Application No. 2007-527511, mailing date of Apr. 26, 2011.

*Primary Examiner* — Ernest G Therkorn
(74) *Attorney, Agent, or Firm* — Waters Technologies Corporation

(57) ABSTRACT

A method and apparatus for monitoring and controlling nanoscale flow rate of fluid in the operating flow path of a HPLC system provide fluid flow without relying on complex calibration routines to compensate for solvent composition gradients typically used in HPLC. The apparatus and method are used to correct the flow output of a typical, analytical-scale (0.1-5 mL/min) HPLC pump to enable accurate and precise flow delivery at capillary (<0.1 mL/min) and nano-scale (<1 μL/min) HPLC flow rates.

4 Claims, 1 Drawing Sheet

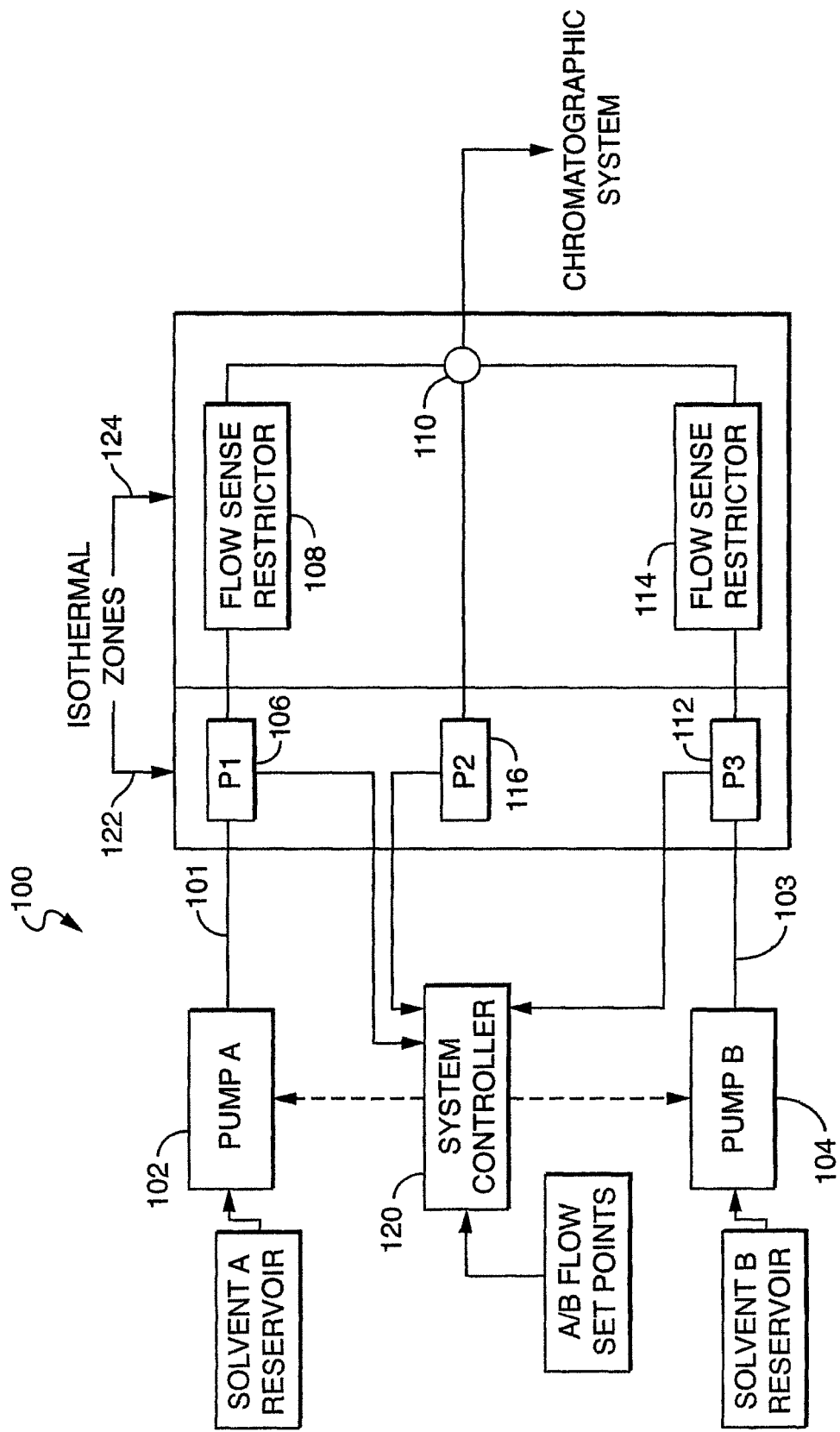

US 8,679,333 B2

CLOSED LOOP FLOW CONTROL OF A HPLC CONSTANT FLOW PUMP TO ENABLE LOW-FLOW OPERATION

CROSS REFERENCE TO RELATED APPLICATIONS

This application is a divisional of application Ser. No. 11/569,301, filed on May 13, 2008, now U.S. Pat. No. 7,674,375, which is the National Stage of International Application No. PCT/US05/17923, filed May 20, 2005, which claims priority to and benefit of Provisional Application Ser. No. 60/573,528, filed May 21, 2004. The entire contents of these applications are incorporated herein by reference.

FIELD OF THE INVENTION

The present invention relates to a flow sensing method and apparatus and more particularly to a flow sensing method and apparatus used to monitor and provide feedback to a closed-loop flow control of an analytical-scale high performance liquid chromatography (HPLC) system which enables the delivery of stable flow to a nano-scale chromatographic system using a micro-scale or normal scale chromatographic pump.

BACKGROUND OF THE INVENTION

The recent interest in nano-scale chromatography (<1 µL/min flow rates) has prompted HPLC instrument manufacturers to try to develop pumps capable of delivering lower flow rates. Unfortunately, typical analytical-scale HPLC pump technology does not scale well to these low flow rates as the constant-flow open-loop analytical-scale pumps typically used for analytical-scale chromatography (0.1-5 mL/min) are good flow sources above ~0.1 µL/min, but below these flow rates, inaccuracies due to solvent compression and seal, fitting or check-valve leakage compromise their flow accuracy.

Traditional plunger displacement pumping systems have been successful in delivering stable, accurate flows in the normal-scale and micro-scale high performance liquid chromatography regimes. While normal-scale HPLC is performed with mobile phase flow rates of about 0.1-5.0 mL/min and micro-scale HPLC is performed with mobile phase flow rates of about 1-100 µL/min, nano-scale HPLC requires mobile phase flow rates in the 50-1000 nL/min range. Current plunger displacement pumping systems typically cannot deliver nano-scale HPLC flow rates with reliability and accuracy.

One method for providing nano-scale flow rates in an HPLC system is to use a flow-divider which directs a majority of flow from the pump to a waste stream and a small portion of the pump output to the HPLC working stream (i.e., to the liquid chromatography column). A split restrictor in the waste stream and/or the working stream controls the split ratio of the system. Normal-scale or micro-scale HPLC pumps can be used in split flow mode to produce nano-scale HPLC flow rates in the working stream.

Unfortunately, in order to operate a HPLC system in split-flow mode the user must calculate the split ratio of the system. To calculate the split ratio, the user must know the permeabilities of both the split restrictor and the chromatographic system (i.e. the packed column). These permeabilities are used to calculate the flow rate that must be supplied by the normal-scale or micro-scale HPLC pump to produce the desired flow through the chromatographic system. Although it is possible to calculate split restrictor dimensions that should provide a desired split ratio, changes in permeability of either the split restrictor or chromatographic column over time cause unpredictable split ratio variations. Such variations result in unacceptable flow variations through the chromatographic column.

One possible solution to the problem of changing split ratios is to monitor the flow to the chromatographic column with an appropriate flow sensor. Fluid flow rates can be determined by measuring the pressure of a liquid flowing through a restrictor. Assuming a constant viscosity, the back pressure of liquid flowing through a restrictor will scale linearly with the flow rate of the liquid. The flow rate is measured by placing a pressure transducer before and after a restrictor inline with the flow. Signals from the pressure transducers are electronically subtracted and amplified to achieve a high degree of common-mode noise rejection.

The permeability of the restrictor is chosen so that it provides sufficient back pressure to produce a measurable pressure difference signal ($\Delta P$) in the flow ranges of interest but does not produce a significant back pressure for the pump. For example, a 10 cm long, 25 µm inside diameter capillary will provide a back pressure of approximately 100 pounds per square inch (psi) for water flowing at 5 µL/min. This permeability is sufficient for providing a flow measurement while not inducing much fluidic load on the pump.

However, pressure measuring flow sensors must be calibrated to compensate for the different viscosity of each fluid being measured. This creates a great disadvantage in liquid chromatography applications wherein fluid composition varies dramatically over the course of a chromatography run.

Another method that can be used to sense fluid flow is thermal flow sensing. Several companies including Sensirion AG, of Zurich, Switzerland, and Bronkhorst Nijverheidsstraat of Ruurlo, The Netherlands, have been developing thermal flow sensors capable of monitoring flows in nL/min ranges.

In the operation of these thermal flow sensors, heat introduced into a liquid filled tube/channel will disperse in both the upstream and downstream directions (i.e. due to thermal conduction or diffusion respectively). The tube of the flow sensing device is made from materials of low thermal conductivity (i.e. glass, plastic). A temperature profile will develop when a discrete section of the fluid in the tube is continuously heated, under a zero flow condition. The shape of this temperature profile will depend upon the amount of heat added to the fluid and the upstream and downstream temperatures of the liquid. Assuming identical upstream and downstream fluid temperatures, under a zero-flow condition, liquid temperatures measured at first and second sensor will be equal as thermal diffusion will be equal in both directions.

If the liquid in the tube is permitted to flow, the fluid temperatures at the first and second sensor will depend upon the rate of liquid flux and the resulting heat convection. As liquid begins to flow past the heated zone, a temperature profile develops. In addition to the symmetric diffusion of the heat, asymmetric convection of the heated fluid will occur in the direction of the fluid flow. Therefore, under flowing conditions, fluid temperatures measured at the first and second sensor will be different.

Temperature measurements made at the first and second sensor are sampled, subtracted and amplified electronically in situ to provide a high degree of common-mode noise rejection. This allows discrimination of extremely small upstream and downstream temperature differences. By appropriate placement of temperature measurement probes (i.e., first and second sensor) and/or by changing the amount of heat added to the flowing liquid, temperature measurement can be made at inflection points along the temperature profile. Measurement at the inflection points maximizes the upstream/downstream ΔT response to flow rate change.

However, like pressure measuring flow sensors which must be calibrated to compensate for the different viscosity of each fluid being measured. Thermal based flow sensors also need such calibration. This at times creates a disadvantage in liquid chromatography applications wherein fluid composition varies dramatically over the course of a chromatography run.

Other pump solutions for creating the low flow rates required by nano-scale LC involve single-stroke syringe pumps. These pumps have a fixed delivery volume. As a result run times may be limited by the length of the pump stroke. Time is required between each run to refill the pump. During this refill cycle, the chromatographic system must depressurize, then re-pressurize to start the next run. Repeated depressurization/re-pressurization cycles unfortunately have a deleterious effect on the chromatographic column.

Additionally, Nano-scale LC systems are often coupled to mass spectrometers. Electro-spray interfaces typically used in LC-coupled mass spectrometers are most stable when constantly flowing. The stop-flow conditions existing during refill cycles of syringe-type pumps as noted above may destabilize the electro-spray mass spectrometry interface.

SUMMARY OF THE INVENTION

Some embodiments of the present invention involve a method and apparatus for monitoring and controlling the nano-scale flow rate of fluid in an operating flow path of a HPLC system without relying on complex calibration routines to compensate for solvent composition gradients typically used in HPLC. According to some of these embodiments of the invention, an apparatus and method is used to correct the flow output of a typical, analytical-scale (0.1-5 mL/min) HPLC pump to enable accurate and precise flow delivery at capillary (<0.1 mL/min) and nano-scale (<1 μL/min) HPLC flow rates.

According to one embodiment of the invention, the analytical-scale constant flow-source HPLC pumps used are modified commercially available pumps. These commercially available pumps are retro-fitted with minor hardware and/or firmware changes to enable low-flow delivery. Typically, analytical-scale HPLC pumps use stepper-motor driven linear actuators. Depending on the pump architecture, the change required to enable low-flow delivery involves modifying the gearing of the pump drive mechanism offering a higher incremental drive resolution. According to one embodiment of the invention, changes to the firmware/stepper motor drive electronics increasing the micro-stepping resolution of the stepper motor drive is contemplated. It is envisioned, for example, that minor modifications to the pumps firmware by increasing the micro-stepping resolution from 10 μSteps to 100 μSteps enables low-flow operation.

In a first illustrative embodiment, delta-P type flow meters, as in-line sensors, are used within the inventive apparatus. Fluid flow from a first pump in an operating path flows through an initial in-line pressure transducer and through a restriction element and is mixed with fluid flow from a second pump within a second operating path having a second in-line sensor and restriction element at a fluidic cross. Pressure at this fluidic cross is measured by a fluidic cross pressure transducer. According to the invention, a pressure drop measured between the first and second inline flow sensors and the pressure at the fluidic cross will be proportional to the flow delivered by the first and second pumps respectively. While delta-P flow sensors typically require two pressure transducers for each flow line, the inventive fluidic cross pressure transducer arrangement allows the fluidic cross transducer to be used by each respective flow line. The use of a common fluidic cross transducer at the fluidic cross eliminates the need for four pressure transducers.

In another illustrative embodiment of the invention, an apparatus for delivering a liquid in a capillary system includes two flow-source pumps and two associated thermal sensors. Advantages of the invention include correction of the flow output of a typical, analytical-scale (0.1-5 mL/min) HPLC pump enabling accurate and precise flow delivery at capillary (<0.1 mL/min) and nano-scale (<1 μL/min) HPLC flow rates. The present invention permits retrofitting and reuse of existing pump technology providing cost and supply advantages.

A further advantage of the inventive apparatus and method is there are significant advantages to reusing existing pump technology with the flow correcting apparatus according to the invention. These advantages include cost savings associated with development, sales and service training and inventory management. Furthermore, traditional constant-flow HPLC pumps are ideally suited for use according to the invention.

Another further advantage of the inventive apparatus and method is because constant flow pumps are used, calibration of the flow sensors can be accomplished easily by flowing know flow rates through the sensors to determine their response. This calibration routine according to the invention can be done at relatively low pressures where pump leakage and solvent compressibility is not an issue, and steady open-loop flow delivery can be expected. Because a known flow rate is being delivered by the constant-flow pumps, the error between this delivered flow and the flow measured by the flow sensors can be used to diagnose pump leakages. Intelligence can be implemented according to the invention to correlate flow error with the pump cycle to identify where leakages were occurring. Advantageously, this level of diagnostics is extremely useful not only for troubleshooting pump failure, but early diagnosis and suggested corrective action to prevent pump failure.

A further advantage of the inventive method and apparatus is continuous flow operation is possible using typical constant-flow HPLC flow sources. Advantageously, all limitations resulting from stop-flow conditions can be avoided.

BRIEF DESCRIPTION OF THE DRAWING

The foregoing and other features and advantages of the present invention will be more fully understood from the following detailed description of illustrative embodiments, taken in conjunction with the accompanying drawing in which:

FIG. 1 is a schematic representation of a closed-loop flow control binary solvent delivery system using temperature stabilized delta-P flow sensors, according to the invention.

DETAILED DESCRIPTION

Detailed embodiments of the present invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention in virtually any appropriately detailed embodiment.

Some embodiments of the invention involve one or more flow sources. A "flow source" is herein understood to be a source that provides a fluid having a flow rate associated with a volume per unit of time. For example, one type of flow source includes a piston that displaces a volume of fluid per unit of time. A particular value of volume per unit of time is determined, for example, by controlling the linear velocity of the piston, and by selecting a piston diameter, in the case of a piston having a circular cross-section. Thus, for example, the velocity of the piston multiplied by the area defines a volumetric flow rate. This flow rate is analogous to, for example, a current source in an electrical circuit, which provides an amount of charge per unit of time.

A flow source is distinct from a pressure source, such as a pneumatic air supply with a regulator. A pressure source is analogous to, for example, a voltage in an electrical circuit. Pressure (voltage, in the analogy) induces a particular flow rate (a current in the analogy) if impressed upon a fluid restriction (a resistor, in the analogy). Thus, while a flow source has the ability to independently determine a flow rate, a pressure source typically does not independently determine a flow rate. Rather, a pressure source works in cooperation with other component(s) of a flow path, such as a flow-restrictor component, to determine a flow rate through the flow path.

Turning to FIG. 1, a schematic of a closed loop system 100 according to the invention is shown. A first pump 102 and a second pump 104, which are flow-source pumps such as, for example, analytical-scale constant flow-source HPLC pumps. These analytical-scale constant flow-source pumps are any suitable pumps such as commercially available pumps (for example, the WATERS® 515, 1525u, and Acquity pumps, available from Waters Corporation, Milford, Mass., USA, or the like.) The first pump 102 and second pump 104 are fitted with minor hardware and/or firmware changes to enable low-flow delivery. Typically, analytical-scale HPLC pumps use stepper-motor driven linear actuators. Depending on the pump architecture, change required to enable low-flow delivery involves modifying the gearing of the pump drive mechanism. These modifications to the gearing of the pump drive mechanism offer a higher incremental drive resolution. It is contemplated within the scope of the invention that changes to the firmware/stepper motor drive electronics to increase the micro-stepping resolution of the stepper motor drive may be used to enable low-flow delivery. In a first illustrative embodiment, minor modifications to the pumps' firmware are made by increasing the micro-stepping resolution from about 10 μSteps to about 100 μSteps. This increased resolution allows low-flow operation.

While it may be possible to develop a pump specifically designed to deliver flow compatible with nano-scale LC, there are significant cost and supply advantages to reusing existing pump technology with the flow correcting apparatus described above. Advantageously, traditional constant-flow HPLC pumps are ideally suited for this application.

With further reference to FIG. 1, the first pump 102 is in fluid communication to a first inline sensor 106. The first inline sensor 106 in a first illustrative embodiment is a delta-P type pressure transducer. In this first illustrative embodiment the pressure transducer used is a DJ model DF Thruflow pressure transducer, DJ Instruments, Billerica, Mass. It is contemplated within the scope of the invention that any flow sensors capable of providing precise and accurate output signals in the micro-scale flow range can be used to implement the flow sensing according to the illustrative embodiment of the invention. In particular, it is contemplated within the scope of the invention that other types of flow sensors may be used including but not limited to thermal-based flow sensors, available from, for example, Bronkhorst High-Tech B.V., Ruurlo, The Netherlands, and Sensirion AG, Zurich, Switzerland.

As shown in FIG. 1, in a first operating path 101 flow from the first pump 102 is in fluid communication with the first inline sensor 106. The first inline sensor 106 is in fluid communication with a first restriction element 108. The first restriction element 108 is in fluid communication with a fluidic cross 110. In a second operating path 103, the second pump 104 is in fluid communication with a second inline sensor 112. The second inline sensor 112 in the first illustrative embodiment is a pressure transducer. The second inline sensor 112 is in fluid communication with a second restriction element 114. The second restriction element 114 is in fluid communication with the fluidic cross 110. Pressure at the fluidic cross 110 is measured by a fluidic cross sensor 116. The fluidic cross sensor 116 in a first illustrative embodiment is a pressure transducer.

In operation, a pressure drop measurement between the first inline sensor 106 and the fluidic cross sensor 116 and the second inline sensor 112 and the fluidic cross sensor 116 will be proportional to the flow delivered by the first pump 102 and the second pump 104 respectively.

While delta-P flow sensors typically require two pressure transducers for each flow line, the inventive configuration having three sensors 106, 112, 116, which in a first illustrative embodiment are pressure transducers, allows the fluidic cross sensor 116 to be used by both operating paths 101, 103. This configuration according to the invention eliminates the need for four pressure transducers. It is contemplated within the scope of the invention, however, that each operating path 101, 103 could have two sensor that are pressure transducers. It is further contemplated within the scope of the invention that each operating path 101, 103 can have only one flow sensor producing a first and second flow signal.

In operation, a system controller 120 will interpret pressures measured by the sensors 106, 112 and 116 using previously obtained calibration constants and calculate flow rates being delivered by the first pump 102 and second pump 104. The system controller 120 will modify flow rates delivered by the pumps 102, 104 to adjust for any error between measured flow rates and set point flow rates. Using the inventive method, flow inaccuracies resulting from solvent compressibility, pump or system leakage are corrected.

In the first illustrative embodiment of the invention, output from the sensors 106, 112, 116 are used to control the flow rate in the respective operating paths 101, 103. FIG. 1 illustrates the first embodiment of the invention where the flow rate in the operating paths 101, 103 is controlled by calculating the pressure drop difference between inline sensors 106, 112 with that of the fluidic cross sensor 116 and adjusting flow rate of the first pump 102 and second pump 104 proportionately. Persons having ordinary skill in the art should appreciate that additional control circuitry (not shown) may be required between the output of the sensors 106, 112, 116 and the input of the pumps 102, 104. For example, additional control circuitry may be implemented to condition the output signal for use as an appropriate control input to the particular pump being used. Circuit components such as buffers, inverters, amplifiers and/or microcontrollers, for example, can be used to implement the control circuitry according to a number of methods that are well known to those skilled in the art.

In the first illustrative embodiment of the invention the controller 120, a microcontroller or microprocessor, is implemented between the pressure transducer output and the control input of the respective pumps 102, 104. The controller 120 can be programmed and configured, for example, to adjust the flow rate of the pumps 102, 104 to a setting appropriate for maintaining a respective flow rate producing a selected gradient composition.

When using delta-P type pressure transducers as flow sensors, in order to obtain accurate flow measurements using differences in the three sensors 106, 112, 116, it is desirable that the zero point of each sensor 106, 112, 116 be maintained at a constant. A common source of zero point drift in strain-gage pressure transducers is transducer temperature fluctuations. Strain-gage pressure transducers measure changes in the resistance of strain elements to determine pressure. The strain element's resistance will also change with temperature. If one or more of the three pressure transducer's, used as sensors 106, 112, 116, zero point changes due to temperature fluctuations, difference calculations used to measure flow rate will be inaccurate. For consistent and reproducible results the three pressure transducers used as sensors 106, 112, 116, in a first illustrative embodiment, may be contained in a first isothermal block 122. In addition, the restriction elements 108, 114 used in conjunction with the sensors 106, 112, 116 may also be maintained in a second isothermal block 124. The temperature of the restriction elements 108, 114 must be maintained at approximately the temperature they were calibrated. Changes in the temperature of the restriction elements 108, 114 will result in erroneous flow measurements as temperature-induced viscosity changes of the fluid inside the restriction elements 108, 114 change the pressure difference across the flow restriction element 108, 114. While the sensors 106, 112, 116 and the flow restriction elements 108, 114 can be maintained at isothermal temperature, it is not necessary that they are maintained at the same temperature.

Flow sensors used in the inventive flow-correcting apparatus will need to be calibrated for the each solvent used in the system. Commercially-based thermal flow sensors have different responses depending on the thermal capacity of the measured fluid. Delta-P type flow sensors are sensitive to solvent viscosity. Because constant flow pumps are used in this system, calibration of these flow sensors can be accomplished easily by flowing known flow rates through the sensors to determine their response. This calibration routine can be done at relatively low pressures where pump leakage and solvent compressibility is not an issue, and steady open-loop flow delivery can be expected.

Because a known flow rate is being delivered by constant-flow pumps, the error between the delivered flow and the flow measured by the flow sensors can be used to diagnose pump leakages. It is contemplated within the scope of the invention that system intelligence can be implemented in the flow controller 120 to correlate flow error within the pump cycle identifying where leakages are occurring. In typical two-plunger reciprocating or serial flow delivery pumps, flow errors can be correlated to the seal or check valve responsible for the leakage. This level of diagnostics allowed by such system intelligence according to the invention is useful for troubleshooting pump failure allowing for early diagnosis and suggested corrective action preventing costly pump failure.

Other pump solutions for creating the low flow rates required by nano-scale HPLC involve single-stroke syringe pumps. These pumps have a fixed delivery volume. As a result run times may be limited by the length of the pump stroke. Time is required between each run to refill the pump. During this refill cycle, the chromatographic system must depressurize, then re-pressurize to start the next run. Repeated depressurization/re-pressurization cycles may have a deleterious effect on the chromatographic column. Nano-scale LC systems are often coupled to mass spectrometers. Electro-spray interfaces, used in LC-coupled mass spectrometers, are most stable when constantly flowing. The stop-flow conditions existing during refill cycles of syringe-type pumps may destabilize the electro-spray mass spectrometry interface. When using the inventive apparatus and method described herein, continuous flow operation is possible using constant-flow HPLC flow sources. Thus all limitations resulting from stop-flow conditions can be avoided.

By using analytical-scale continuous flow HPLC pumps, high flow rates can be used to prime the system when solvent change over is necessary. For nano-flow systems that employ low-flow only pumps, this priming operation may take a significant amount of time.

Although sensors are described herein in terms of specific pressure-type, delta-P, flow sensors or thermal base flow sensors, persons skilled in the art should appreciate that any number of various flow sensor types may be substituted therefor without departing from the spirit and scope of the present invention. For example several types of commercially available sensors or the like can be used as in-line flow sensors according to the present invention. Likewise in embodiments using sensors other than pressure-type sensors, each flow path may contain a singular flow sensor controlling the output of its respective pump or pressure source.

Although flow sensors are described herein in terms of being in fluid communication with a flow sense restrictor, persons skilled in the art should appreciate that the sensors described herein may be used without flow sense restrictors without departing from the spirit and scope of the present invention.

In another illustrative embodiment of the invention, a system optionally includes fewer components than the embodiment described above with reference to FIG. 1. This alternative system includes two flow-source pumps and two associated thermal sensors. Flow restrictors and a cross sensor are not, however, included in this alternative embodiment.

This alternative embodiments has several potential advantages. For example, parasitic losses that at times arise due to pressure-type sensors are avoided.

Although various embodiments of the present invention are described herein in terms of separate circuit components for comparing pressure from various sensor components, persons skilled in the art should appreciate that a single circuit component can be implemented to serve multiple comparison functions according to the present invention. For example, a single microcontroller having multiple measurement input ports and control output ports can be used to receive and process first pressure drop and second pressure drop signals to compute desired path flow rates and generate output signals for communicating to the first and second pumps. An application specific integrated circuit (ASIC) could also be designed, for example, to perform these functions as well as incorporating the functions of the pumps, either by digital or analog operation, without departing from the spirit and scope of the present invention.

Although embodiments of the present invention are described herein which control flow rates in the respective operating paths by controlling the pump, persons skilled in the art should appreciate that these various control elements could be also implemented in various combinations according to the present invention.

Although the various embodiments of the present invention are described for use in measuring nano-scale flow rates in an HPLC system, persons skilled in the art should appreciate that the present invention can be used to measure and control a variety of different capillary systems, or fluid control and analysis systems without departing from the spirit and scope of the invention.

Although the invention is described hereinbefore with respect to illustrative embodiments thereof, persons having ordinary skill in the art should appreciate that the foregoing and various other changes, omissions and additions in the form and detail thereof may be made without departing from the spirit and scope of the invention.

What is claimed is:

1. An apparatus for delivering a liquid in a chromatography capillary system comprising:
   a first pump in fluid communication to a first flow path carrying a first portion of a liquid from said first pump to a first thermal-based flow sensor contained within an isothermal block, said first thermal-based flow sensor being operatively disposed in said first flow path and configured to produce a first signal corresponding to a flow rate of said first pump;
   a second pump in fluid communication to a second flow path carrying a second portion of a liquid from said second pump to a second thermal-based flow sensor contained within said isothermal block, said second thermal-based flow sensor being operatively disposed in said second flow path and configured to produce a second signal corresponding to a flow rate of said second pump; and
   means for controlling flow rates within each flow path in response to said first and second flow-rate signals, the means for adjusting comprising a system controller configured to adjust the flow rates of said first and second pumps proportionately.

2. The apparatus according to claim 1 wherein the first pump comprises a a first flow source, and the second pump comprises a second flow source.

3. The apparatus of claim 2 wherein the first flow source comprises a piston.

4. The apparatus of claim 3 wherein the first flow source is configured to provide a particular flow rate in response to a velocity of the piston and a surface area of the piston.

* * * * *